(12) United States Patent
Abdelgany et al.

(10) Patent No.: US 8,002,807 B2
(45) Date of Patent: Aug. 23, 2011

(54) SEALED LUBRICATION SYSTEM AND METHOD FOR DYNAMIC STABILIZATION SYSTEM

(75) Inventors: Mahmoud F. Abdelgany, Rockaway, NJ (US); YoungHoon Oh, Montville, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 462 days.

(21) Appl. No.: 12/348,284

(22) Filed: Jan. 3, 2009

(65) Prior Publication Data
US 2010/0174313 A1    Jul. 8, 2010

(51) Int. Cl.
*A61B 17/70*    (2006.01)
(52) U.S. Cl. ........ 606/264; 606/246; 606/257; 606/266; 606/300; 606/301; 623/17.11
(58) Field of Classification Search .......... 606/246–279, 606/300–321; 623/17.11
See application file for complete search history.

(56) References Cited

U.S. PATENT DOCUMENTS

| | | | |
|---|---|---|---|
| 6,554,831 B1 | 4/2003 | Rivard et al. | |
| 6,692,529 B2 | 2/2004 | Shah | |
| 6,966,910 B2 | 11/2005 | Ritland | |
| 7,361,196 B2 | 4/2008 | Fallin et al. | |

*Primary Examiner* — Eduardo C Robert
*Assistant Examiner* — Christina Negrelli
(74) *Attorney, Agent, or Firm* — Rahman LLC

(57) ABSTRACT

A dynamic screw assembly includes a fixation component that connects to a vertebral body, the fixation component includes at least one inlet to allow a lubricant to pass inside the fixation component, a ring member coupled to the fixation component, a stopper sealing at least one inlet, a coupling member includes an inwardly curved bottom portion and a bulbous end extending from the inwardly curved bottom portion, a bumper mechanism coupled to the fixation component and the coupling member, a longitudinal member coupled to the coupling member, and a blocker that retains the longitudinal member in the coupling member. The bulbous end includes at least one groove that houses the lubricant, and at least one slot to allow the bulbous end to fit into the fixation component and to limit a range of angulation of the coupling member with respect to the fixation component.

20 Claims, 13 Drawing Sheets

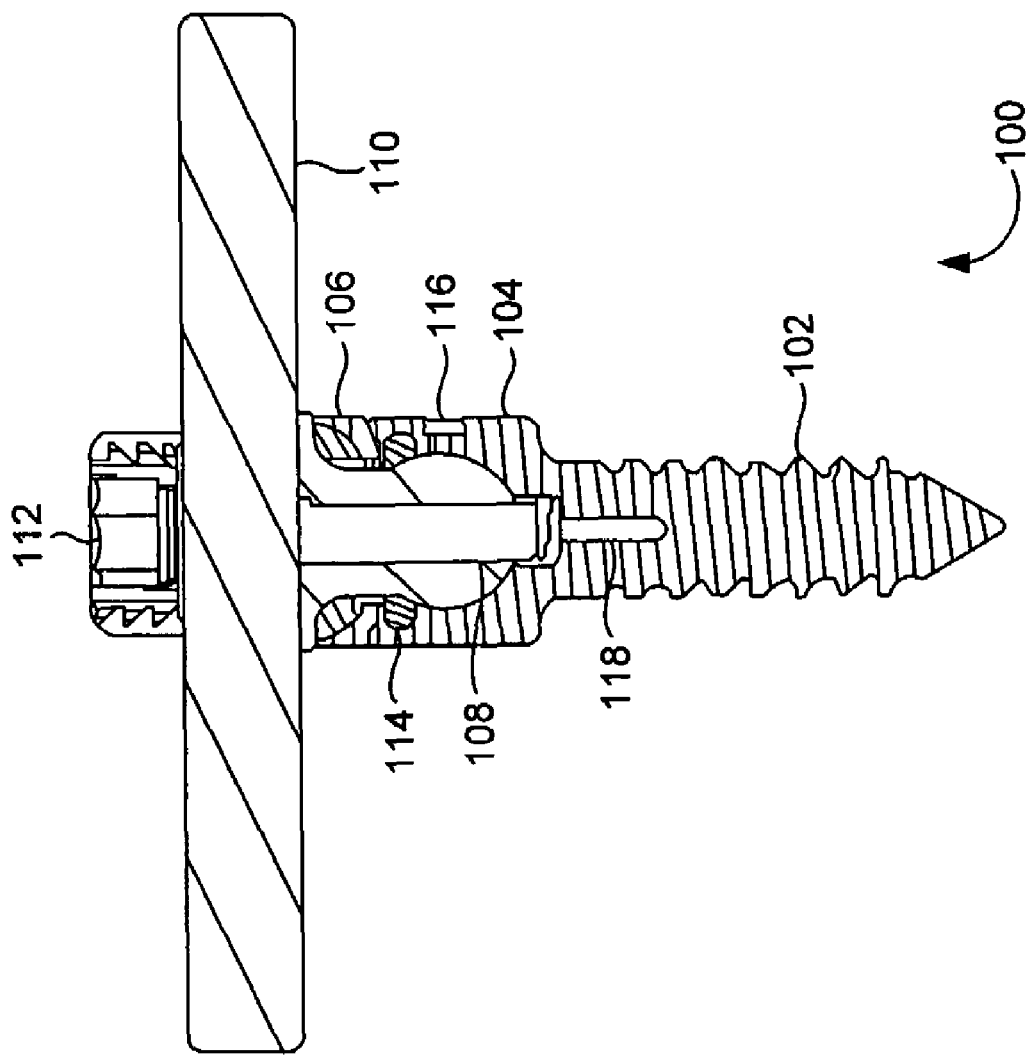

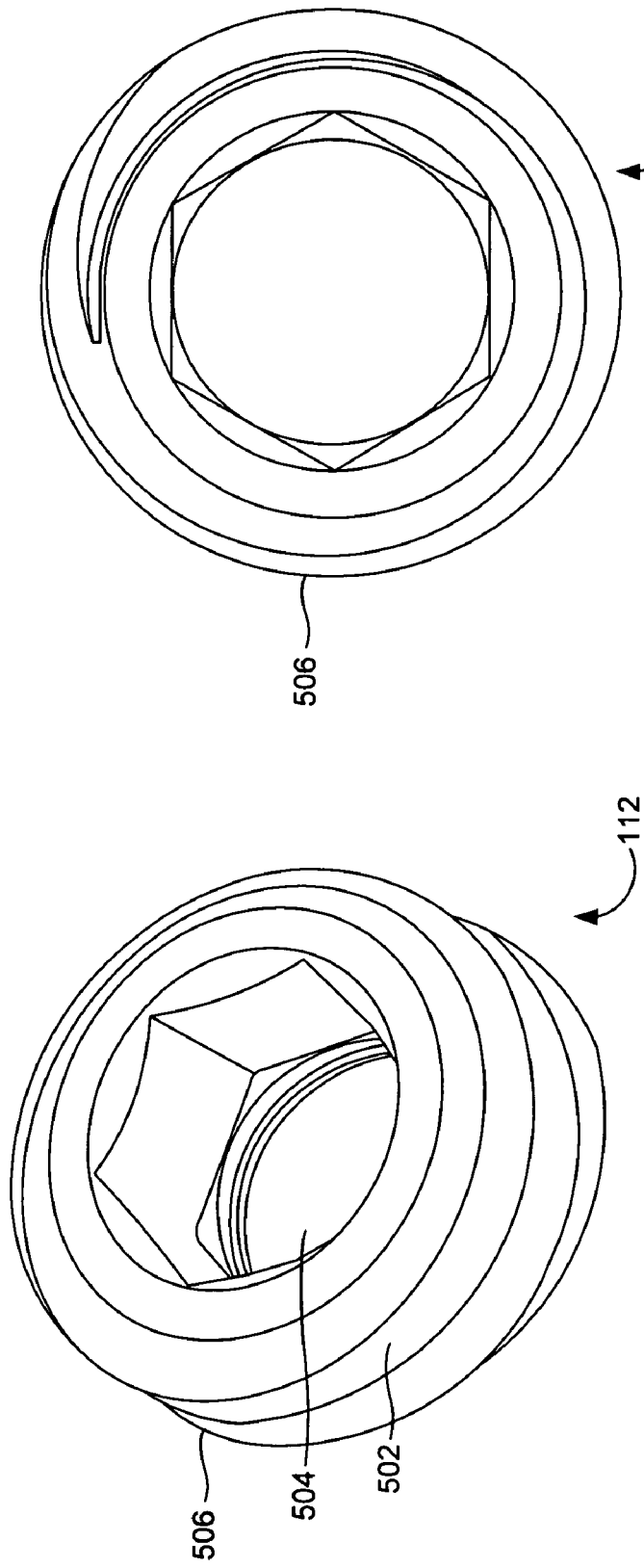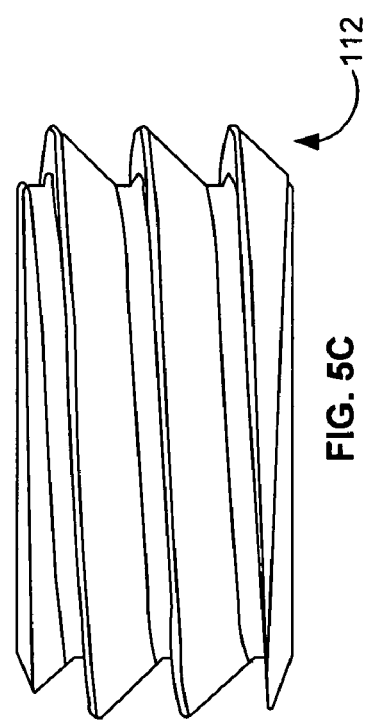
FIG. 5B
FIG. 5C
FIG. 5A

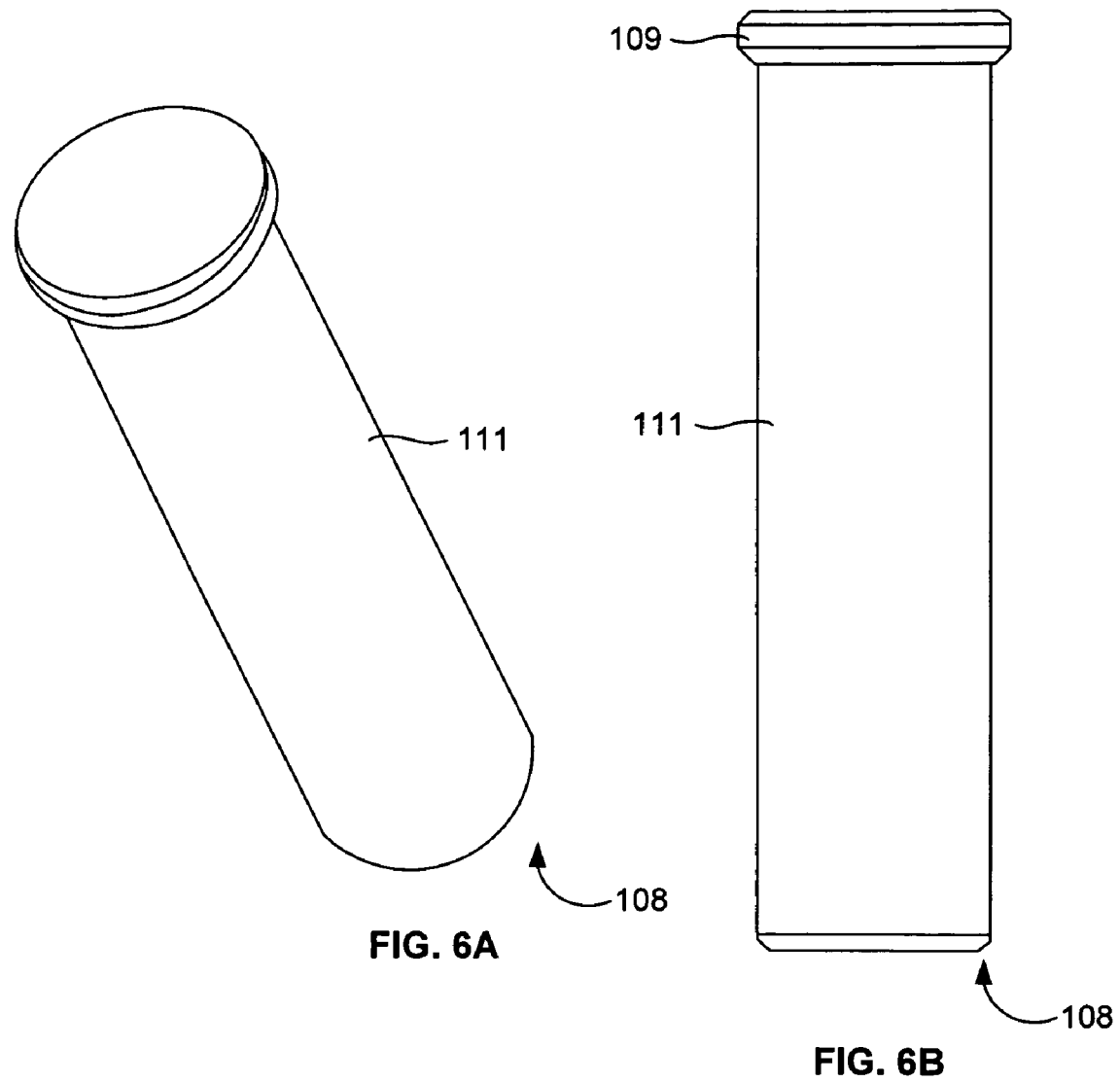
FIG. 6A
FIG. 6B
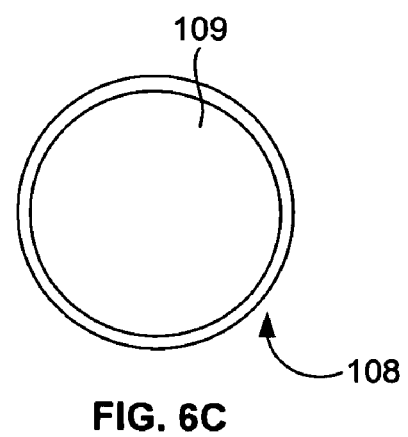
FIG. 6C

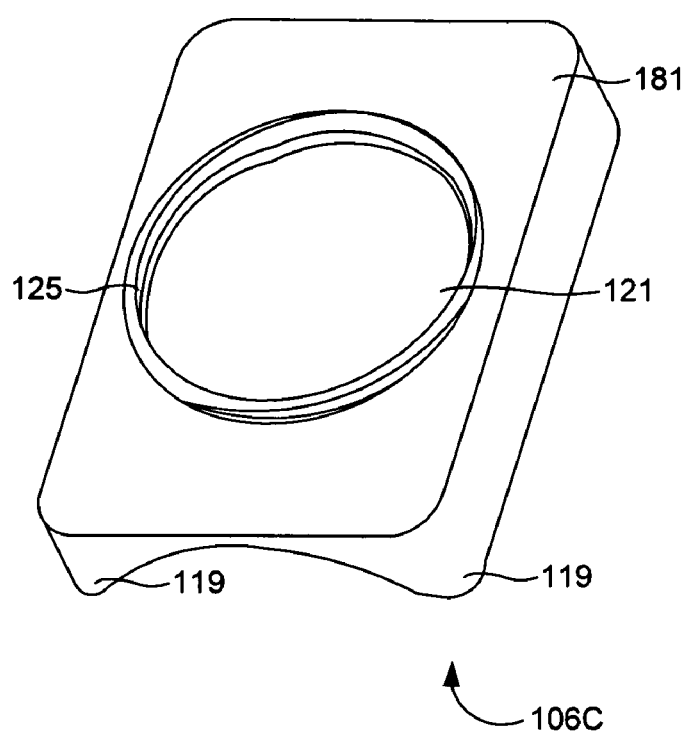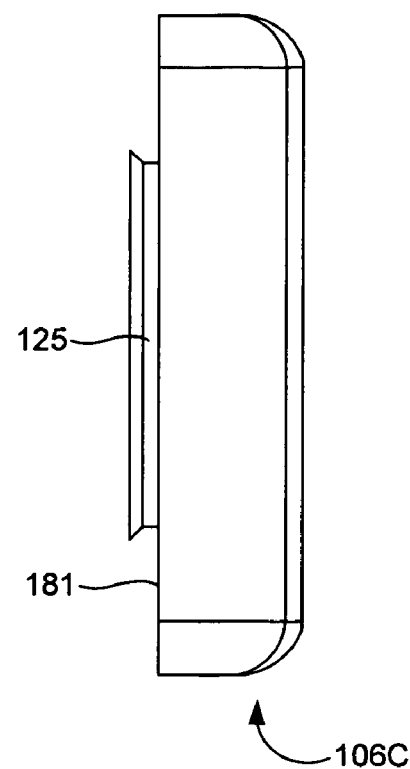
FIG. 9A
FIG. 9B
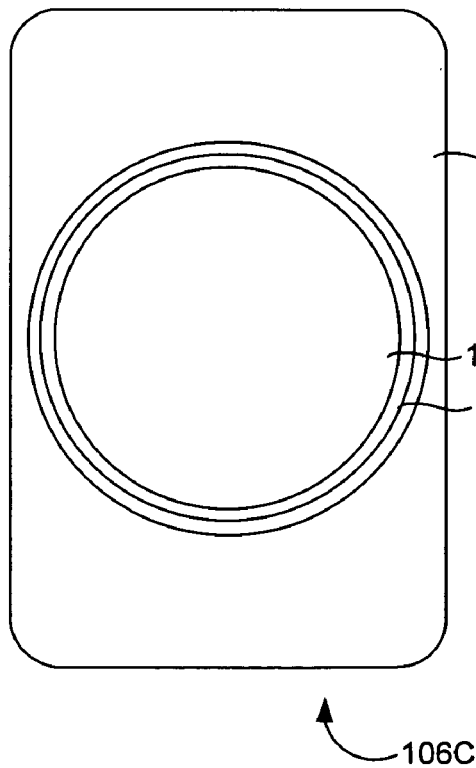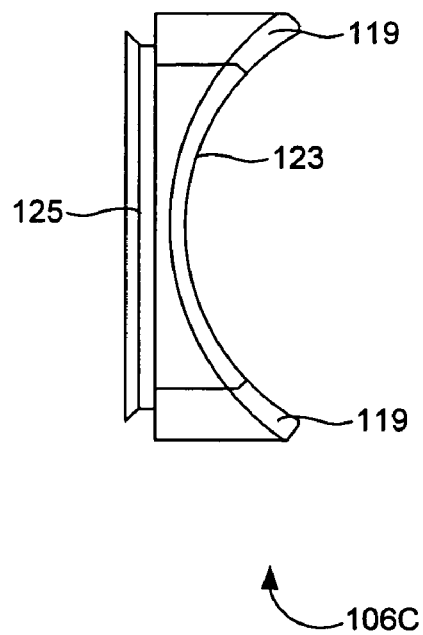
FIG. 9D
FIG. 9C

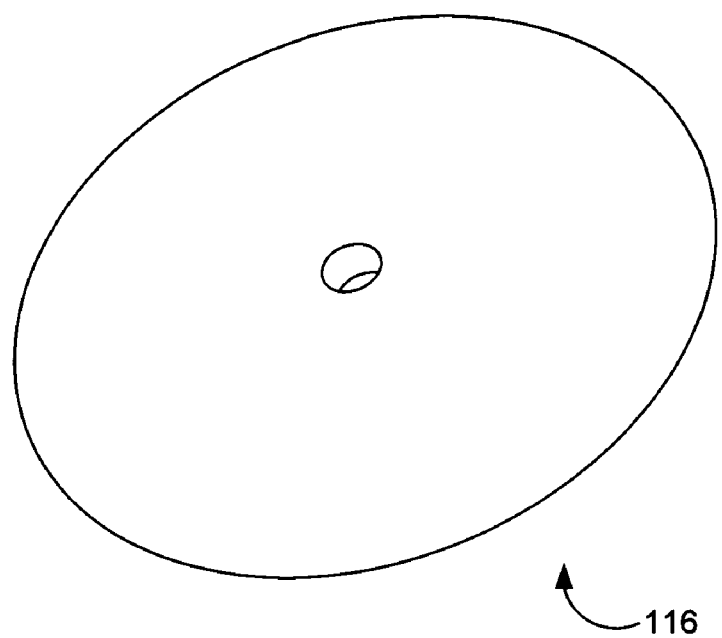
FIG. 11A
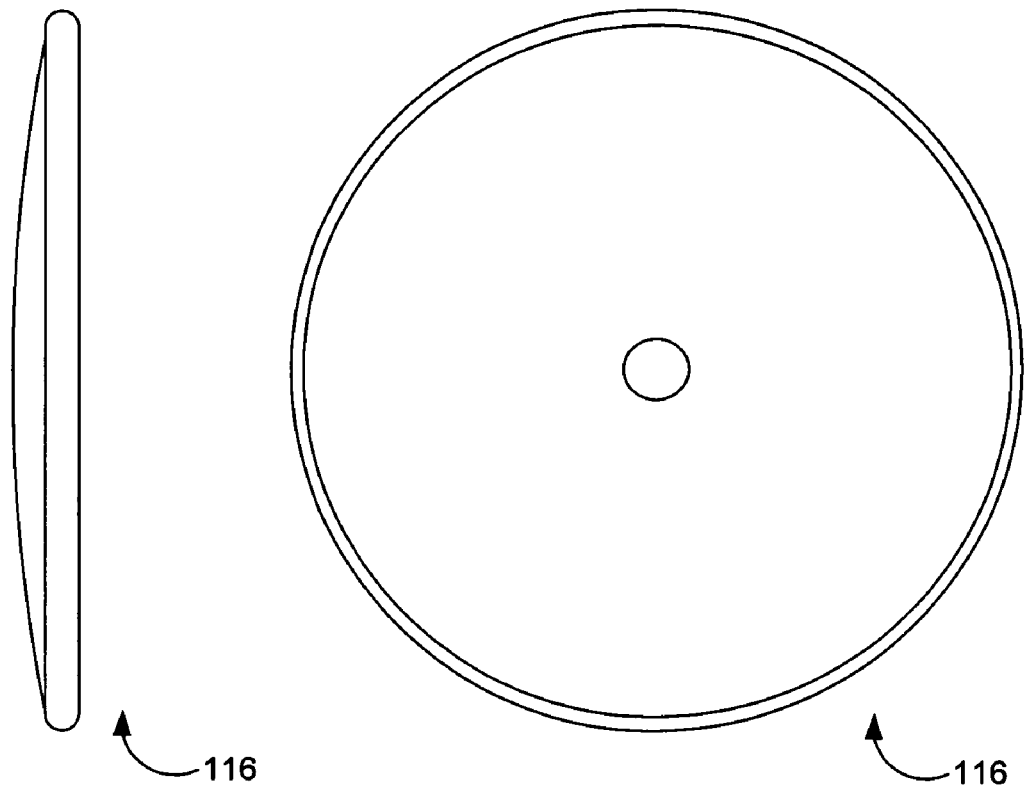
FIG. 11B      FIG. 11C

SEALED LUBRICATION SYSTEM AND METHOD FOR DYNAMIC STABILIZATION SYSTEM

BACKGROUND

1. Technical Field

The embodiments herein generally relate to a dynamic stabilization system, and, more particularly, to a sealed lubrication system for a dynamic stabilization system.

2. Description of the Related Art

Intervertebral disc degeneration often leads to chronic lower back pain. This may be due to abnormal loading patterns on the disc. Degenerative disc disease may be treated by restricting the motion of the spine to a range where near normal disc loading occurs. Rigid spinal instrumentation restricts the motion but alters the loading environment of the disc away from the dynamic stabilization systems. Systems such as inter spinous process spacers, pedicle screws, and facet replacement products are hence used to maintain the ideal physiologic state of the disc. In dynamic stabilization systems, there is movement between components of the system along with natural movements of the spine. This leads to a lot of wear and tear due to friction between the rough base materials of the dynamic stabilization systems.

SUMMARY

In view of the foregoing, an embodiment herein provides a dynamic screw assembly including a fixation component that connects to a vertebral body, the fixation component includes at least one inlet to allow a lubricant to pass inside the fixation component, a ring member coupled to the fixation component, a stopper sealing at least one inlet, a coupling member includes an inwardly curved bottom portion and a bulbous end extending from the inwardly curved bottom portion, a bumper mechanism coupled to the fixation component and the coupling member, a longitudinal member coupled to the coupling member, and a blocker that retains the longitudinal member in the coupling member. The ring member prevents the lubricant from leaking out of the fixation component. The bulbous end includes at least one groove that houses the lubricant, and at least one slot to allow the bulbous end to fit into the fixation component and limit a range of angulation of the coupling member with respect to the fixation component.

A saddle connection is inserted through the bulbous end of the coupling member and may be extended to the fixation component, and a spring member coupled to the saddle connection. The spring member provides a continuous upward force on the saddle connection. The saddle connection prevents disengaging of the coupling member from the fixation component. The longitudinal member connects to a plurality dynamic screw assemblies.

The lubricant is inserted between the fixation component and the coupling member. The groove houses the lubricant. The fixation component includes a reservoir to hold the lubricant. The reservoir may be positioned in one of a location of the spring member and on a side of the fixation component. The coupling member includes a U-shaped slot positioned between a pair of opposite arms. The U-shaped slot accommodates the longitudinal member.

Another embodiment herein provides an apparatus for dynamic stabilization of a vertebral column. The apparatus includes a lubricant having material properties that reduce friction and increase wear resistance of objects in connection with the lubricant, a bone anchor including an open concave head, an inlet, and a groove, a ring member coupled to the bone anchor, a coupling member including a pair of arms that are diametrically opposed, the pair of arms including a U-shaped slot positioned between the pair of arms and an inwardly curved bottom portion of the coupling member, and an outwardly protruding and expandable bulbous end extending from the inwardly curved bottom portion, and a hole positioned extending from the inwardly curved bottom portion and through the bulbous end, a bumper mechanism coupled to the fixation component and the coupling member, a saddle connection that is engaged in the hole of the coupling member and connects to the bone anchor, a longitudinal member engaged in the U-shaped slot, a spring member coupled to the saddle connection, a stopper connected to the bone anchor, and a threaded blocker that engages the pair of arms of the coupling member and secures the longitudinal member in the U-shaped slot.

The inlet allows the lubricant to pass inside the bone anchor. The ring member prevents leakage of the lubricant from the groove. The bulbous end is seated inside the open concave head of the bone anchor. The bumper mechanism is shaped to accommodate a predetermined range of angulation of the fixation component with respect to the coupling member. The spring member continuously pushes up the engaged saddle connection. The stopper seals the lubricant in the groove of the bone anchor.

The open concave head of the bone anchor includes an inner portion that receives the bulbous end of the coupling member, a circular groove, a gap that engages the saddle connection, and an outer circular portion. The pair of arms includes an outer wall including an indent feature, and an inner wall including threads. The circular groove engages the ring member. The outer circular portion includes an opening that engages the stopper.

Yet another embodiment provides a method of assembling a dynamic screw system. The method includes attaching a coupling member to a bone fixation component, inserting a lubricant in an aperture, inserting a ring member in a groove, engaging a bumper between the bone fixation component and the coupling member, securing a saddle connection in the opening, inserting a longitudinal member in a U-shaped slot, and engaging a blocker in the pair of arms and against the longitudinal member.

A stopper may be inserted in the aperture. The stopper prevents the lubricant from escaping from the bone fixation component. The longitudinal member may be connected to a plurality of dynamic screw assemblies. A spring member may be positioned inside the bone fixation component and against the saddle connection. The spring member provides a continuous upward force on the saddle connection. The bone fixation component includes a reservoir positioned in at least one of a location of the spring member and on a side of the bone fixation component to house the lubricant. The bulbous end includes at least one groove to house the lubricant. The blocker retains the longitudinal member in the coupling member.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 1A through 1C illustrate a cross-sectional view, a side view, and a top view, respectively, of a dynamic screw assembly according to an embodiment herein;

FIGS. 5A through 5C illustrate a perspective view, a top view, and a front view, respectively, of the blocker of the dynamic screw assembly of FIGS. 1A through 1C according to an embodiment herein;

FIGS. 6A through 6C illustrate a perspective view, a front view, and a top view, respectively, of the saddle connection of the dynamic screw assembly of FIGS. 1A through 1C according to an embodiment herein;

FIGS. 9A through 9D illustrate a perspective view, a front view, a cross-sectional view, and a top view, respectively, of the bumper of the dynamic screw assembly of FIGS. 1A through 1C according to a third embodiment herein;

FIGS. 11A through 11C illustrate a perspective view, a front view, and a top view, respectively, of the stopper of the dynamic screw assembly of FIGS. 1A through 1C according to an embodiment herein.

DETAILED DESCRIPTION OF EMBODIMENTS

Figure 1C:
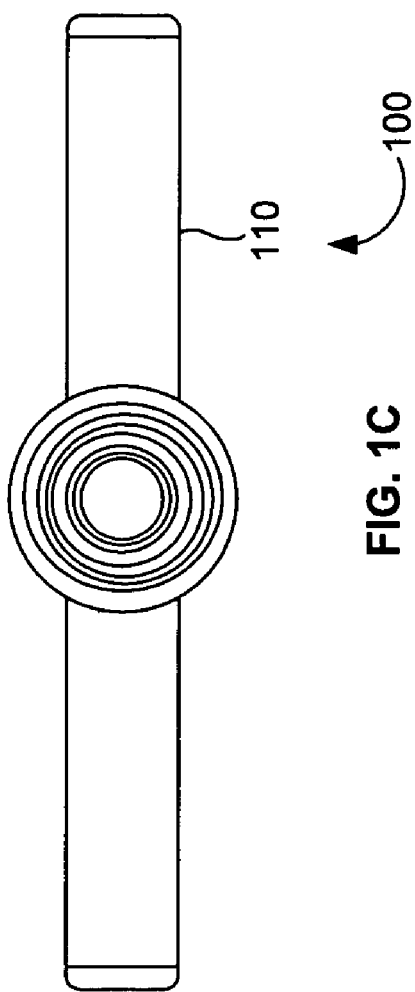

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a lubrication system stored and sealed in a dynamic screw assembly that provides minimal leakage, decreases friction, and improves wear resistance. Referring now to the drawings, and more particularly to FIGS. 1A through 12, where similar reference characters denote corresponding features consistently throughout the figures, there are shown preferred embodiments.

Figure 1B:
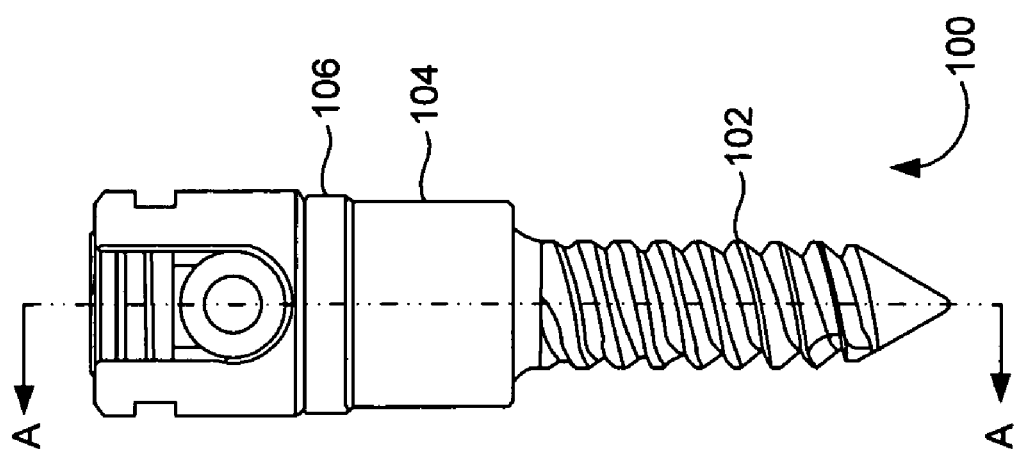
Figure 2A:
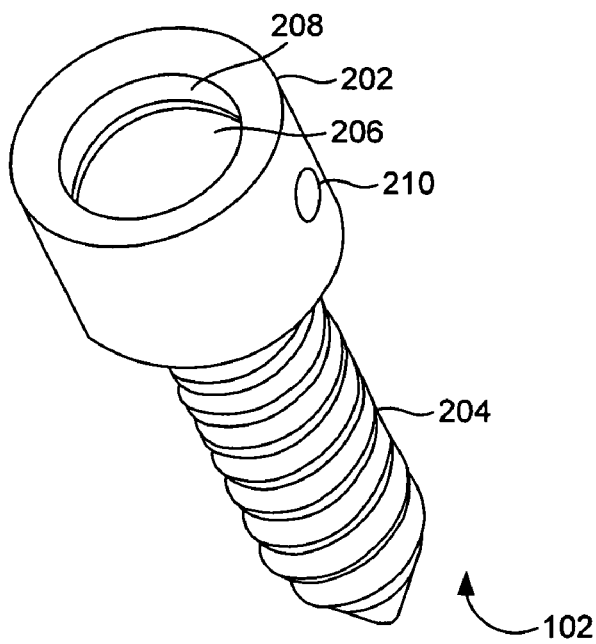
FIGS. 2A through 2D illustrate a perspective view, and a front view, a cross-sectional view, and a top view, respectively, of the bone anchor of the dynamic screw assembly of FIGS. 1A through 1C according to an embodiment herein.
Figure 2B:
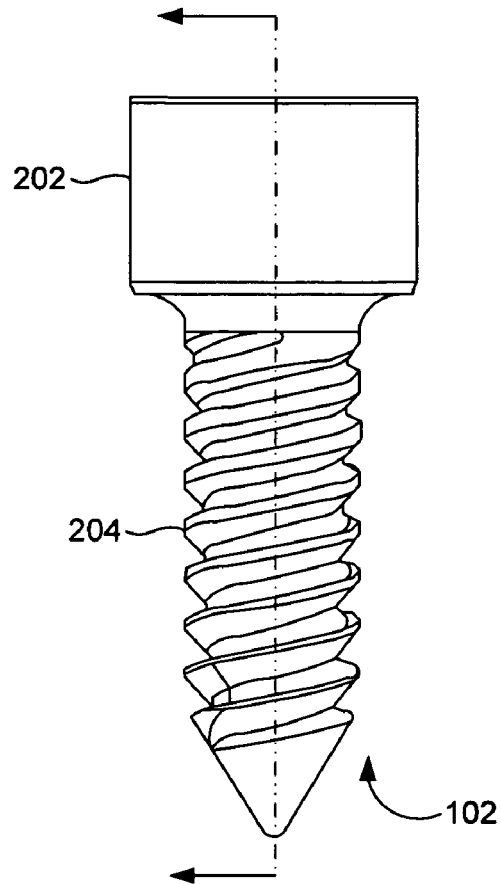
Figure 2C:
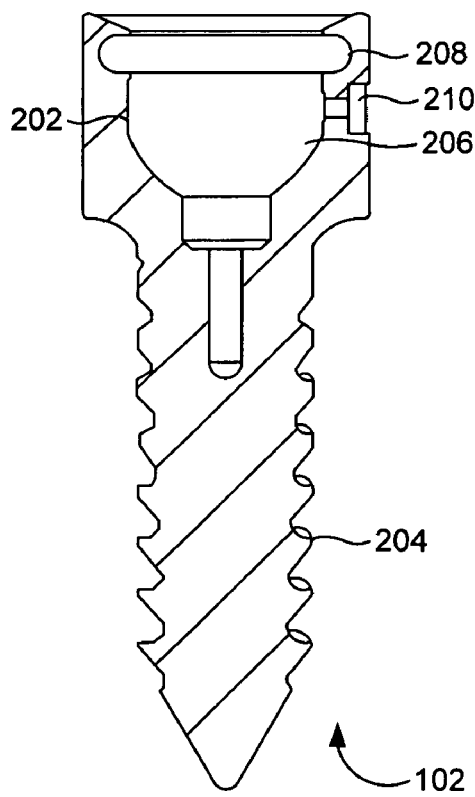
Figure 2D:
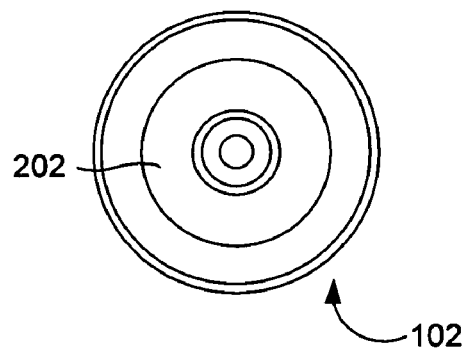
Figure 3A:
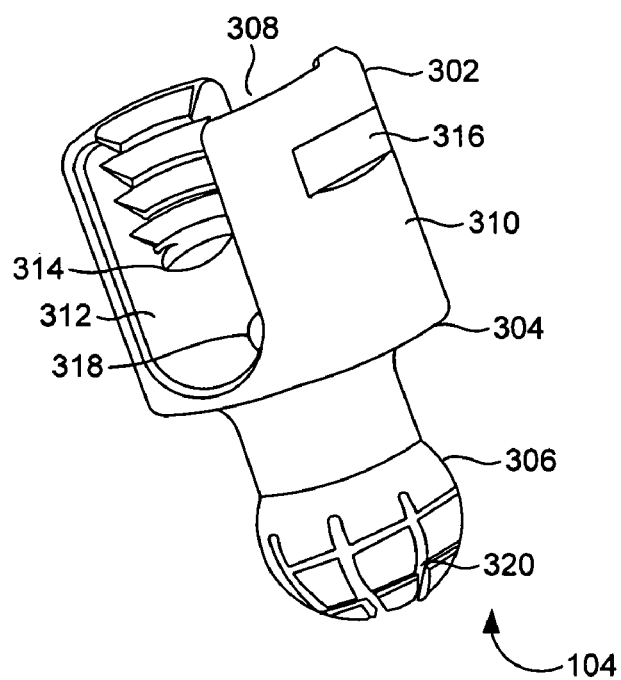
FIGS. 3A through 3D illustrate a perspective view, a front view, a cross-sectional view, and a top view, respectively, of the coupling member of the dynamic screw assembly of FIGS. 1A through 1C according to an embodiment herein.
Figure 3B:
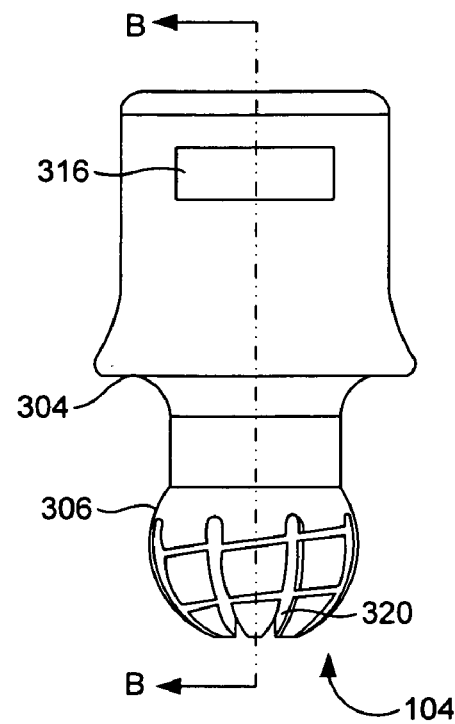
Figure 3D:
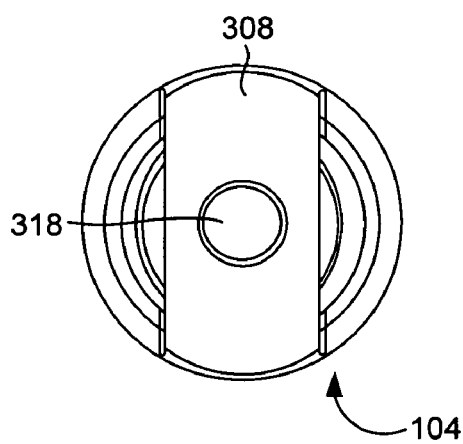
Figure 3C:
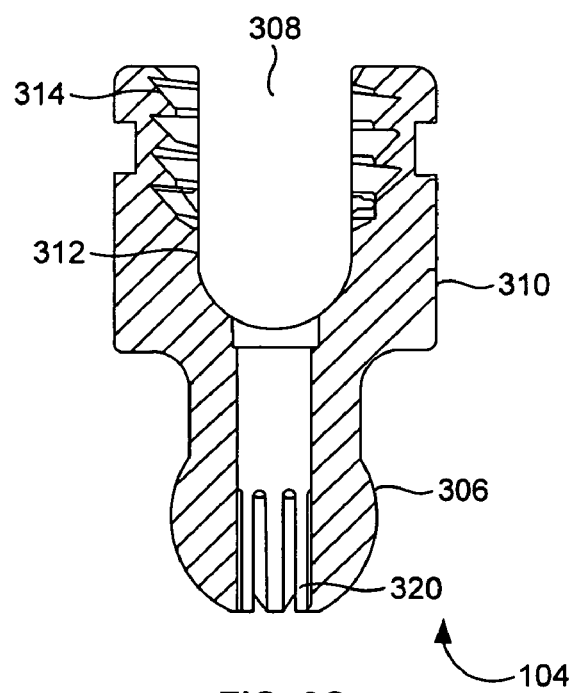

FIGS. 1A through 1C illustrate a sectional view, a side view, and a top view, respectively, of a dynamic screw assembly 100 according to an embodiment herein. The dynamic screw assembly 100 includes a bone anchor 102, a coupling member 104, a bumper 106, a saddle connection 108, a rod 110, a blocker 112, a ring member 114, a stopper 116, and a spring member 118. The bone anchor 102 is embodied as a fixation component to be inserted into a bone (not shown). The top portion of the bone anchor 102 may be angled to accept the bumper 106. The coupling member 104 is embodied as a screw head connecting the bone anchor 102 and the rod 110.

The bumper 106 is located between the bone anchor 102 and the coupling member 104. In one embodiment, the bumper 106 is shaped to coincide with the range of angulation created by the dynamic screw assembly 100. The saddle connection 108 may be placed along a vertical axis through the center of the coupling member 104 to prevent the coupling member 104 from disengaging the bone anchor 102. The rod 110 is embodied as a longitudinal member positioned along a horizontal axis in the coupling member 104 to connect the coupling member 104 and the saddle connection 108.

The blocker 112 is the securing member to retain the rod 110 in the coupling member 104 and pushes down onto the saddle connection 108 to effectively lock the dynamic screw assembly 100. The ring member 114 is located on top of the bone anchor 102 and prevents a lubricant from escaping. The stopper 116 is inserted in the bone anchor 102 to prevent the lubricant from leaking out. The spring member 118 is located on a bottom of the bone anchor 102 and continuously pushes up the saddle connection 108. A lubricant (not shown) is inserted between the bone anchor 102 and the coupling member 104 to reduce friction and increase wear resistance. The lubricant may be natural lubricants (blood, fat, etc.) or an artificial substance (mineral oil, etc.).

FIGS. 2A through 2D illustrate a perspective view, and a front view, a cross-sectional view, and a top view, respectively, of the bone anchor 102 of the dynamic screw assembly 100 of FIGS. 1A through 1C according to an embodiment herein. With reference to FIGS. 1A through 2D, the bone anchor 102 includes an open concave head 202 and a threaded portion 204. The open concave head 202 of the bone anchor 102 may be angled to accept the bumper(s) 106. The open concave head 202 further includes an inner portion 206, a circular groove 208, and an opening 210 on an outer circumference of the open concave head 202.

The inner portion 206 of the open concave head 202 receives the coupling member 104 and the saddle connection 108. The circular groove 208 accommodates the ring member 114. The lubricant is inserted inside the bone anchor 102 through the opening 210 and the stopper 116 is inserted in the opening 210 on the outer circumference of the open concave head 202 to seal the lubricant and prevent leakage. In one embodiment, the bone anchor 102 has a plurality of openings for allowing the lubricant to go into the bone anchor 102.

FIGS. 3A through 3D illustrate a perspective view, a front view, a cross-sectional view, and a top view, respectively, of the coupling member 104 of the dynamic screw assembly 100 of FIGS. 1A through 1C according to an embodiment herein. With reference to FIGS. 1A through 3D, the coupling member 104 is embodied as a screw head and connects to the bone anchor 102 and the rod 110. The coupling member 104 includes a pair of arms 302, an inwardly curved bottom portion 304, a bulbous end 306, and a U-shaped slot 308. The arms 302 further include an outer wall 310 and an inner wall 312.

The outer wall 310 of the arms 302 includes an indent feature 316. The inner wall 312 includes threads 314 to engage the blocker 112. The coupling member 104 also has an opening 318 through the middle of the inwardly curved bottom portion 304 and extending through the bulbous end 306. The bulbous end 306 includes channels 320 to allow the bulbous end 306 to become flexible and expandable. The U-shaped slot 308 is positioned between the arms 302 to receive the rod 110. The indent feature 316 on the outer wall 310 of the coupling member 104 may be configured for various instruments (not shown) to manipulate the bone anchor 102 during a surgery.

In one embodiment, the channels 320 of the bulbous end 306 allow the coupling member 104 to be inserted to the bone anchor 102 through the bottom portion 304 and limit range of angulation. The opening 318 receives the saddle connection 108 and allows the saddle connection 108 to be fixed firmly to the bone anchor 102. In another embodiment, the bulbous end 306 of the coupling member 104 can have groove(s) (not shown) for the lubricant to fill up. This space (e.g., the groove) may be utilized as a self-reservoir for the lubricant. The groove (not shown) may hold the lubricant to reduce friction and increase wear resistance.

Figure 4A:
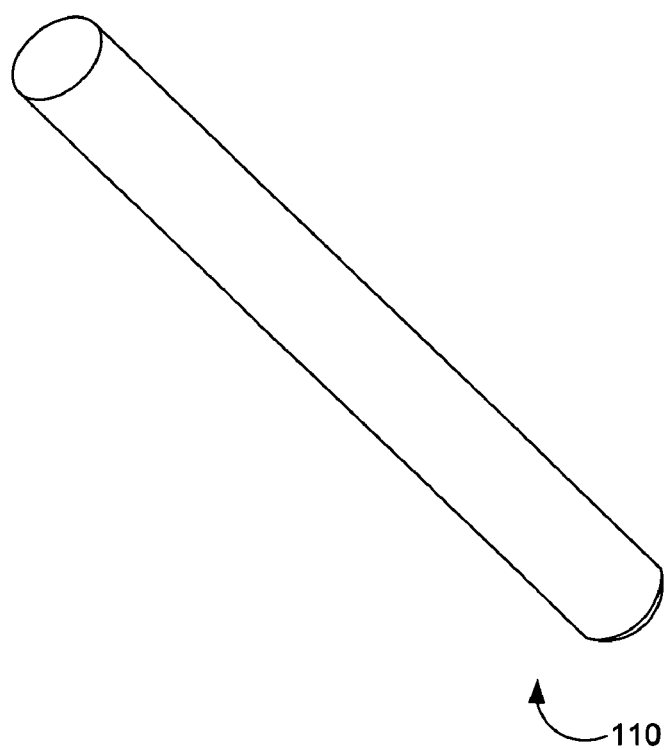
FIGS. 4A through 4C illustrate a perspective view, a front view, and a top view, respectively, of the rod of the dynamic screw assembly of FIGS. 1A through 1C according to an embodiment herein.
Figure 4B:
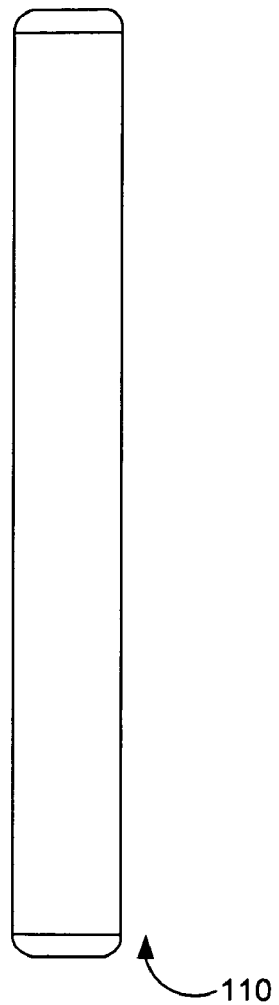
Figure 4C:
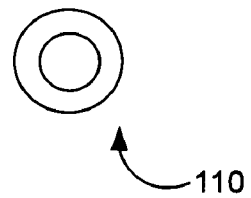
Figure 7A:
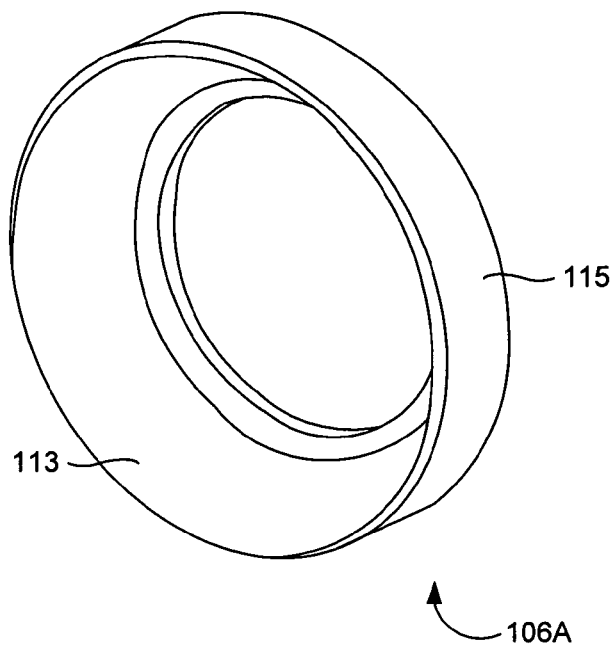
FIGS. 7A through 7D illustrate a perspective view, a front view, a cross-sectional view, and a top view, respectively, of the bumper of the dynamic screw assembly of FIGS. 1A through 1C according to a first embodiment herein.
Figure 7B:
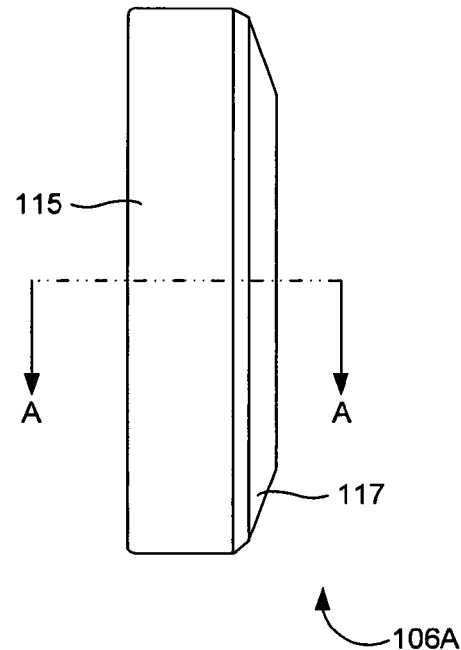
Figure 7D:
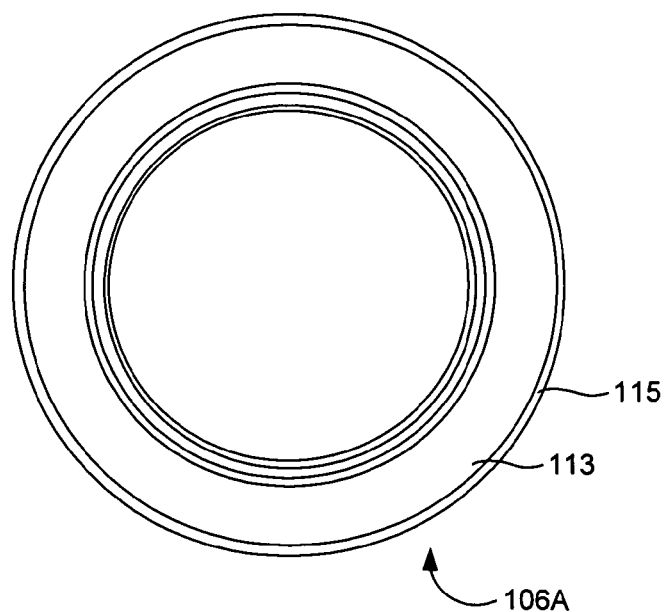
Figure 7C:
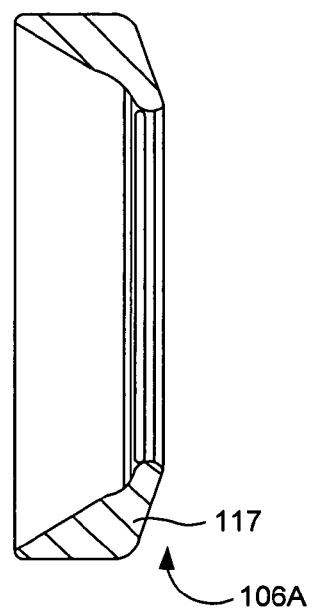
Figure 8A:
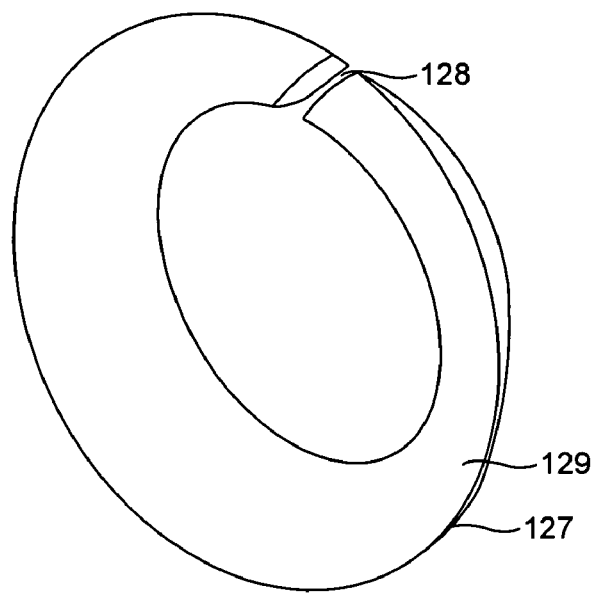
FIGS. 8A through 8D illustrate a perspective view, a front view, a cross-sectional view, and a top view, respectively, of the bumper of the dynamic screw assembly of FIGS. 1A through 1C according to a second embodiment herein.
Figure 8B:
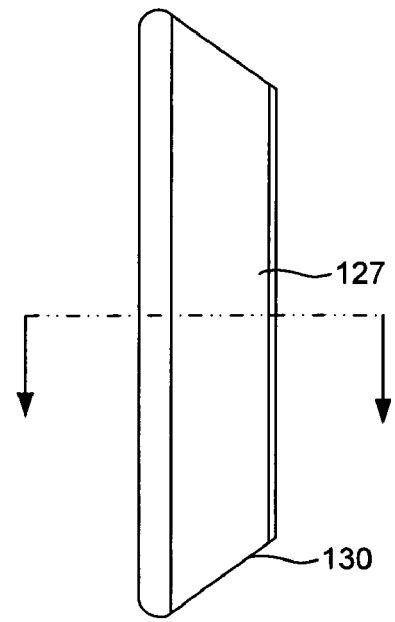
Figure 8D:
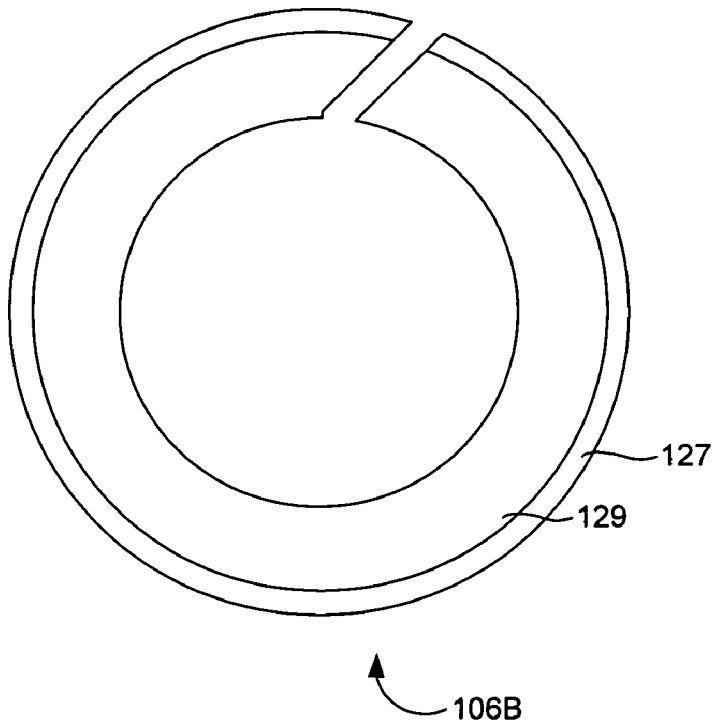
Figure 8C:
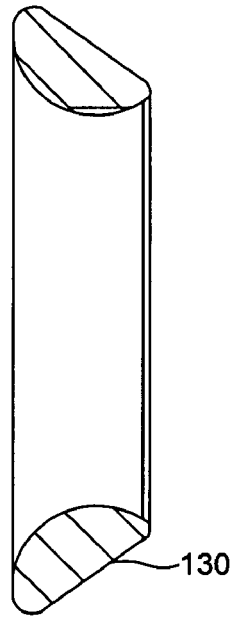
Figure 10A:
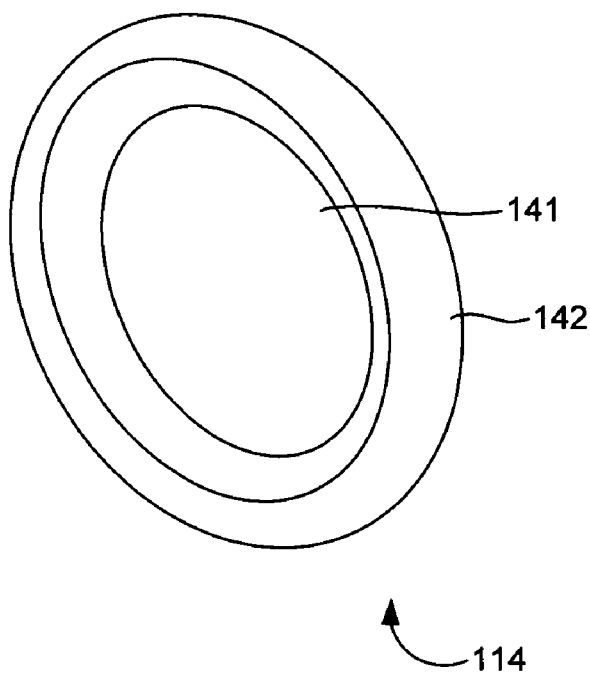
FIGS. 10A through 10D illustrate a perspective view, a front view, a cross-sectional view, and a top view, respectively, of the ring member of the dynamic screw assembly of FIGS. 1A through 1C according to an embodiment herein.
Figure 10B:
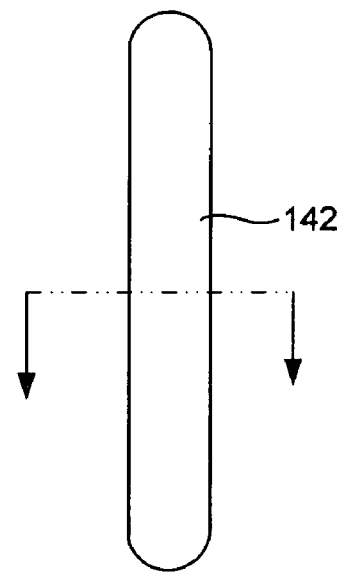
Figure 10D:
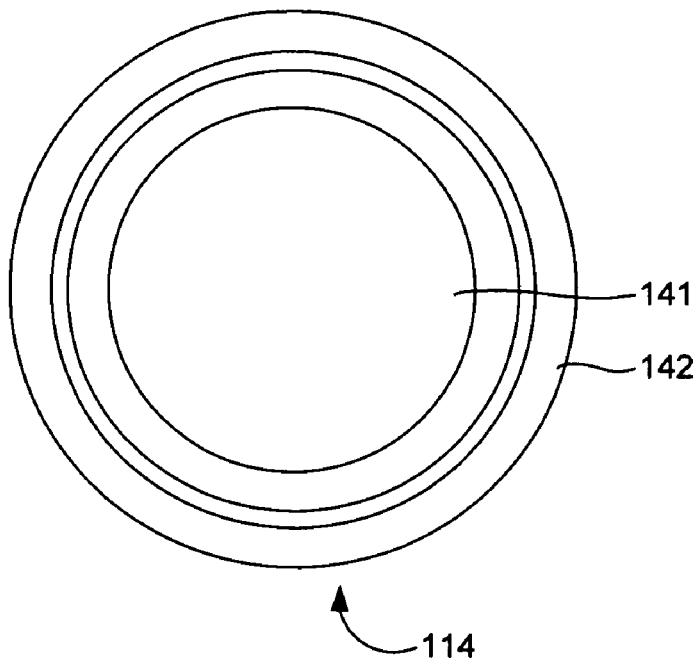
Figure 10C:
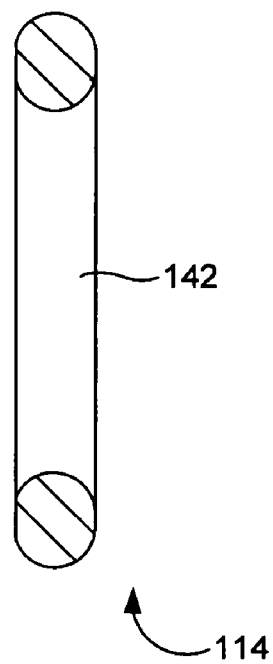

FIGS. 4A through 4C illustrate a perspective view, a front view, and a top view, respectively, of the rod 110 of the dynamic screw assembly 100 of FIGS. 1A through 1C according to an embodiment herein. With reference to FIGS. 1A through 4C, the rod 110 is embodied as a longitudinal member connecting the coupling member 104 and the saddle connection 108. The rod 110 is positioned longitudinally in the U-shaped slot 308 of the coupling member 104. In one embodiment, the rod 110 is a connecting member between multiple dynamic screw assemblies.

FIGS. 5A through 5C illustrate a perspective view, a top view, and a front view, respectively, of the blocker 112 of the dynamic screw assembly 100 of FIGS. 1A through 1C according to an embodiment herein. With reference to FIGS. 1A through 5C, the blocker assembly 112 is the securing means for the rod 110 to the coupling member 104, and, indirectly, to allow the coupling member 104 to be secured to the bone anchor 102. The blocker assembly 112 includes an outer cylindrical parameter 502 and a hexagonal aperture 504 in the middle. The outer cylindrical parameter 502 includes threads 506 to push down on the rod 110 that pushes down onto the saddle connection 108 effectively locking the dynamic screw assembly 100. Any appropriate configuration of the blocker assembly 112 may be used in accordance with the embodiments herein.

FIGS. 6A through 6C illustrate a perspective view, a front view, and a top view, respectively, of the saddle connection 108 of the dynamic screw assembly 100 of FIGS. 1A through 1C according to an embodiment herein. With reference to FIGS. 1A through 6D, the saddle connection 108 is embodied as a longitudinal member with a head portion 109 circumferentially larger than the circumference of the body portion 111 of the saddle connection 108. The saddle connection 108 is placed along a vertical axis through the opening 318 of the coupling member 104 to prevent the coupling member 104 from disengaging the bone anchor 102.

FIGS. 7A through 7D illustrate a perspective view, a front view, a cross-sectional view, and a top view, respectively, of the bumper 106 of the dynamic screw assembly 100 of FIGS. 1A through 1C according to a first embodiment herein. In this embodiment, the biased bumper 106A is configured as a bowl-shaped mechanism 115 with an open top 113 and bottom 117. The top 113 bottom 117 of the biased bumper 106 may be beveled to provide the biasing effect.

FIGS. 8A through 8D illustrate a perspective view, a front view, a cross-sectional view, and a top view, respectively, of the bumper 106 of the dynamic screw assembly 100 of FIGS. 1A through 1C according to a second embodiment herein. In this embodiment, the biased bumper 106B is configured as a bowl-shaped mechanism 127 with an open top and bottom. A slot 128 is included in the mechanism 127. The upper surface 129 and lower surface 130 of the biased bumper 106C may be angled to provide the biasing effect.

FIGS. 9A through 9D illustrate a perspective view, a front view, a cross-sectional view, and a top view, respectively, of the bumper 106 of the dynamic screw assembly 100 of FIGS. 1A through 1C according to a third embodiment herein. In this embodiment, the biased bumper 106C comprises a generally flat top portion 181 with a central bore 121 having a raised surface 125 extending outwardly from the top portion 181. A curved bottom portion 123 of the bumper 106C is defined by opposed curved legs 119, which provides the biasing effect.

The biased bumper 106 is located between the bone anchor 102 and the coupling member 104. In one embodiment, the bumper 106 coincides with the range of angulation created by the dynamic screw assembly 100.

FIGS. 10A through 10D illustrate a perspective view, a front view, a cross-sectional view, and a top view, respectively, of the ring member 114 of the dynamic screw assembly 100 of FIGS. 1A through 1C according to an embodiment herein. The ring member 114 fits into the circular groove 208 of the bone anchor 102 and prevents the lubricant from escaping. The ring member 114 includes an open center 141 and an outer circular wall 142. FIGS. 11A through 11C illustrate a perspective view, a front view, and a top view, respectively, of the stopper 116 of the dynamic screw assembly 100 of FIGS. 1A through 1C according to an embodiment herein. In one embodiment, the stopper 116 is disc-shaped and is press fitted into the opening 210 of the bone anchor 102 to seal the lubricant in the bone anchor 102 and prevent the lubricant from leaking out.

The embodiments herein provide a dynamic screw assembly 100 having a sealed lubricant combined with a dynamic screw system allowing the bone to move dynamically with reduced friction and improved wear resistance. The lubricant is stored in a reservoir in the bone anchor 102 and sealed with a stopper 116 so as to prevent it from leaking out from the screw system. This lubrication system with a minimal leakage from the dynamic screw assembly 100 is ideal for a long-term solution of bone-to-bone dynamic movement after the surgery.

Figure 12:
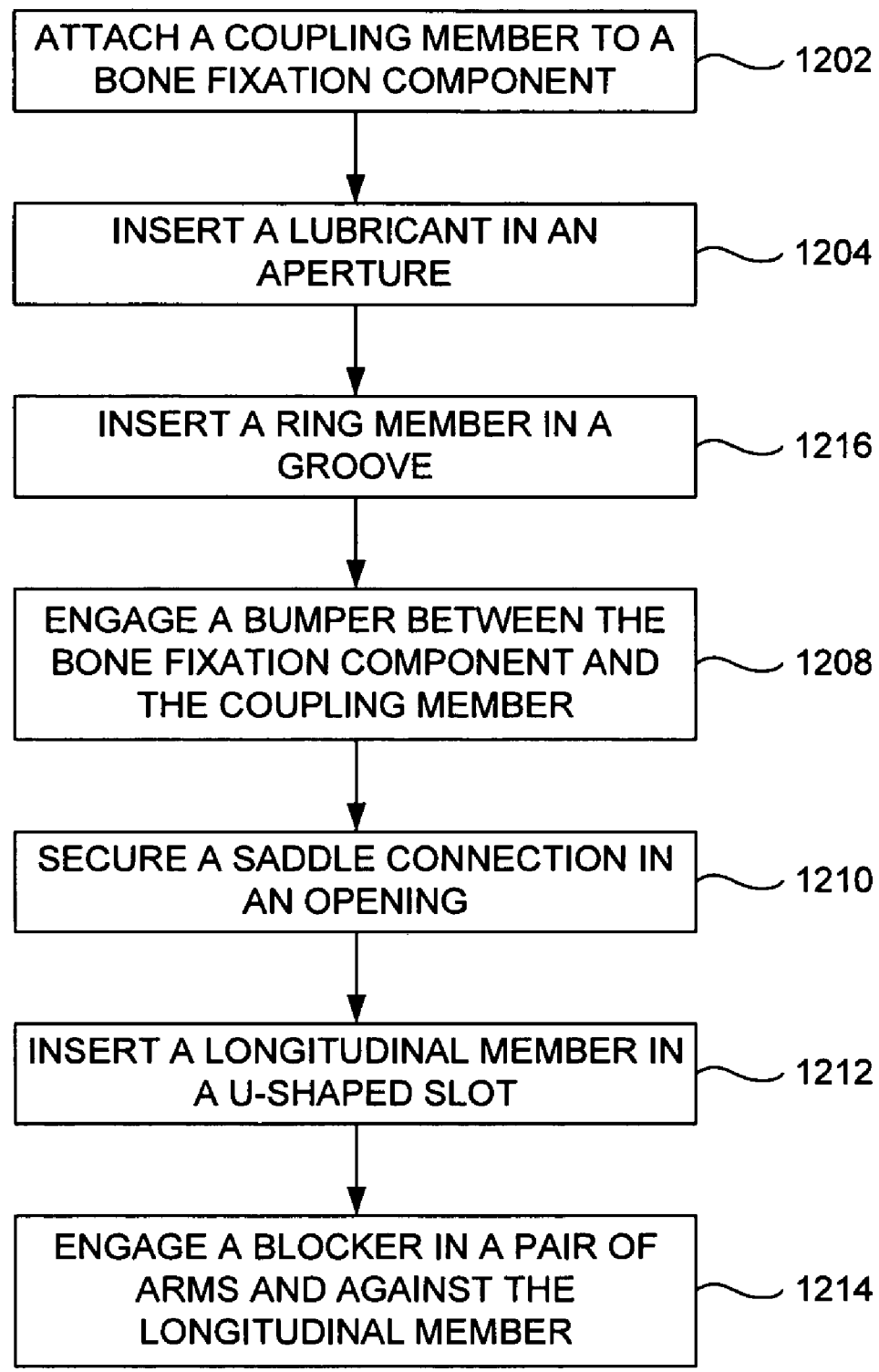
FIG. 12 is a flow diagram illustrating a method of assembling the dynamic screw system of FIGS. 1A through 1C according to an embodiment herein.

FIG. 12, with reference to FIGS. 1 through 11C, is a flow diagram illustrating a method of assembling the dynamic screw system 100 of FIG. 1 according to an embodiment herein. In step 1202, the coupling member 104 is attached to a bone fixation component. The bone fixation component includes a groove 208 and an aperture 504. The coupling member 104 includes a U-shaped slot 308 positioned between a pair of arms 302, an inwardly curved bottom surface, an outwardly protruding bulbous end 306 extending from the inwardly curved bottom surface, and an opening positioned between the inwardly curved bottom surface and the outwardly protruding bulbous end 306.

In step 1204, a lubricant is inserted in the aperture 504. In step 1206, a ring member is inserted in the groove 208. In step 1208, a bumper mechanism 106 is engaged between the bone fixation component and the coupling member 104. The bumper mechanism 106 is shaped to accommodate a predetermined range of angulation of the bone fixation component with respect to the coupling member 104. In step 1210, a saddle connection 108 is secured in the opening. In step 1212, a longitudinal member is inserted in the U-shaped slot 308. In step 1214, a blocker 112 is engaged in the pair of arms 302 and against the longitudinal member.

The stopper 116 may be inserted in the aperture 504. The stopper 116 prevents the lubricant from escaping from the bone fixation component. The longitudinal member may be connected to a plurality of dynamic screw assemblies. A spring member 118 may be positioned inside the bone fixation component and against the saddle connection 108. The spring member 118 provides a continuous upward force on the saddle connection 108. The bone fixation component includes a reservoir positioned in at least one of a location of the spring member 118 and on a side of the bone fixation component to house said lubricant. The bulbous end 306 includes at least one groove 208 to house the lubricant. The blocker 112 retains the longitudinal member in the coupling member 104.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A dynamic screw assembly comprising:
    a fixation component that connects to a vertebral body, said fixation component comprising at least one inlet to allow a lubricant to pass inside said fixation component;
    a ring member coupled to said fixation component, wherein said ring member prevents said lubricant from leaking out of said fixation component;
    a stopper sealing said at least one inlet;
    a coupling member comprising an inwardly curved bottom portion and a bulbous end extending from said inwardly curved bottom portion, wherein said bulbous end comprises:
        at least one groove that houses said lubricant; and
        at least one slot to allow said bulbous end to fit into said fixation component and to limit a range of angulation of said coupling member with respect to said fixation component;
    a bumper mechanism coupled to said fixation component and said coupling member, wherein said bumper is shaped to coincide with said range of angulation;
    a longitudinal member coupled to said coupling member; and
    a blocker that retains said longitudinal member in said coupling member.

2. The dynamic screw assembly of claim 1, further comprising:
    a saddle connection inserted through said bulbous end of said coupling member and extending to said fixation component, wherein said saddle connection prevents disengaging of said coupling member from said fixation component; and
    a spring member coupled to said saddle connection, wherein said spring member provides a continuous upward force on said saddle connection.

3. The dynamic screw assembly of claim 1, wherein said longitudinal member connects to a plurality dynamic screw assemblies.

4. The dynamic screw assembly of claim 1, wherein said lubricant is inserted between said fixation component and said coupling member.

5. The dynamic screw assembly of claim 1, wherein said at least one groove houses said lubricant.

6. The dynamic screw assembly of claim 1, wherein said fixation component further comprises a reservoir to hold said lubricant, said reservoir positioned in at least one of a location of said spring member and on a side of said fixation component.

7. The dynamic screw assembly of claim 1, wherein said coupling member further comprises a U-shaped slot positioned between a pair of opposite arms, and wherein said U-shaped slot accommodates said longitudinal member.

8. An apparatus for dynamic stabilization of a vertebral column, said apparatus comprising:
    a lubricant having material properties that reduce friction and increase wear resistance of objects in connection with said lubricant;
    a bone anchor comprising an open concave head, an inlet, and a groove, wherein said inlet allows said lubricant to pass inside said bone anchor;
    a ring member coupled to said bone anchor, wherein said ring member prevents leakage of said lubricant from said groove;
    a coupling member comprising:
        a pair of arms that are diametrically opposed, said pair of arms comprising a U-shaped slot positioned between said pair of arms and an inwardly curved bottom portion of said coupling member; and
        an outwardly protruding and expandable bulbous end extending from said inwardly curved bottom portion, wherein the bulbous end is seated inside said open concave head of said bone anchor; and
        a hole positioned extending from said inwardly curved bottom portion and through said bulbous end;
    a bumper mechanism coupled to said fixation component and said coupling member, wherein said bumper mechanism is shaped to accommodate a predetermined range of angulation of said fixation component with respect to said coupling member;
    a saddle connection that is engaged in said hole of said coupling member and connects to said bone anchor;
    a longitudinal member engaged in said U-shaped slot;
    a spring member coupled to said saddle connection, wherein said spring member continuously pushes up the engaged saddle connection;
    a stopper connected to said bone anchor, wherein said stopper seals said lubricant in said groove of said bone anchor; and
    a threaded blocker that engages said pair of arms of said coupling member and secures said longitudinal member in said U-shaped slot.

9. The apparatus of claim 8, wherein said open concave head of said bone anchor further comprises:
- an inner portion that receives said bulbous end of said coupling member;
- a circular groove;
- a gap that engages said saddle connection; and
- an outer circular portion.

10. The apparatus of claim 8, wherein said pair of arms comprises:
- an outer wall comprising an indent feature; and
- an inner wall comprising threads.

11. The apparatus of claim 9, wherein said circular groove engages said ring member.

12. The apparatus of claim 9, wherein said outer circular portion comprises an opening that engages said stopper.

13. A method of assembling a dynamic screw system, said method comprising:
- attaching a coupling member to a bone fixation component, wherein said bone fixation component comprises a groove and an aperture, and wherein said coupling member comprises:
  - a U-shaped slot positioned between a pair of arms;
  - an inwardly curved bottom surface;
  - an outwardly protruding bulbous end extending from said inwardly curved bottom surface; and
  - an opening positioned between said inwardly curved bottom surface and said outwardly protruding bulbous end;
- inserting a lubricant in said aperture;
- inserting a ring member in said groove;
- engaging a bumper between said bone fixation component and said coupling member, wherein said bumper mechanism is shaped to accommodate a predetermined range of angulation of said bone fixation component with respect to said coupling member;
- securing a saddle connection in said opening;
- inserting a longitudinal member in said U-shaped slot; and
- engaging a blocker in said pair of arms and against said longitudinal member.

14. The method of claim 13, further comprising inserting a stopper in said aperture.

15. The method of claim 14, wherein said stopper prevents said lubricant from escaping from said bone fixation component.

16. The method of claim 13, further comprising connecting said longitudinal member to a plurality of dynamic screw assemblies.

17. The method of claim 13, further positioning a spring member inside said bone fixation component and against said saddle connection, wherein said spring member provides a continuous upward force on said saddle connection.

18. The method of claim 13, wherein said bone fixation component further comprises a reservoir positioned in at least one of a location of said spring member and on a side of said bone fixation component to house said lubricant.

19. The method of claim 13, wherein said bulbous end further comprises at least one groove to house said lubricant.

20. The method of claim 13, wherein said blocker retains said longitudinal member in said coupling member.

* * * * *